United States Patent [19]
Fertel et al.

[11] Patent Number: 5,405,995
[45] Date of Patent: Apr. 11, 1995

[54] DIFLUOROPHTHALIC COMPOUNDS AND THEIR PREPARATION

[75] Inventors: Lawrence B. Fertel, Williamsville; James J. Maul, Grand Island, both of N.Y.

[73] Assignee: Occidental Chemical Corporation, Niagara Falls, N.Y.

[21] Appl. No.: 262,675

[22] Filed: Jun. 20, 1994

[51] Int. Cl.$^6$ .............................................. C02C 51/00
[52] U.S. Cl. .................................. 562/483; 562/480; 549/246
[58] Field of Search .................. 562/480, 483; 549/246

[56] References Cited

U.S. PATENT DOCUMENTS

| | | | |
|---|---|---|---|
| 4,374,267 | 2/1983 | Fifolt et al. | 562/479 |
| 4,935,541 | 6/1990 | O'Reilly et al. | 562/479 |
| 4,937,377 | 6/1990 | Fertel et al. | 562/456 |
| 5,200,556 | 4/1993 | Papenfuhs et al. | 562/480 |
| 5,294,738 | 3/1994 | Stults et al. | 562/483 |
| 5,322,954 | 6/1994 | Seper et al. | 549/246 |

FOREIGN PATENT DOCUMENTS

| | | |
|---|---|---|
| 9217067 | 5/1992 | Australia . |
| 514863 | 11/1925 | European Pat. Off. . |
| 91/16308 | 10/1991 | WIPO . |

OTHER PUBLICATIONS

Okazaki K et al Synth Commun (1987) 17(9) 1021–7.

*Primary Examiner*—Paul J. Killos
*Attorney, Agent, or Firm*—Wayne A. Jones; Richard D. Fuerle

[57] ABSTRACT

Disclosed are novel compounds having the formula

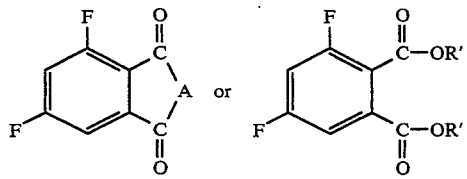

where A is O or NR, each R' independently selected from hydrogen, R, or M, R is alkyl, aryl, alkaryl, or aralkyl from $C_1$ to $C_{12}$, and M is a cation. Also disclosed is a method of making those compounds and a method of making a mixture of 3,5-difluorobenzoic acid and 1,3-difluorobenzene by reacting 3,5-dichlorophthalic anhydride with a fluorinating agent to produce 3,5-difluorophthalic anhydride, reacting the 3,5-difluorophthalic anhydride with water to produce 3,5-difluorophthalic acid, and decarboxylating the 3,5-difluorophthalic acid.

20 Claims, No Drawings

DIFLUOROPHTHALIC COMPOUNDS AND THEIR PREPARATION

BACKGROUND OF THE INVENTION

This invention relates to certain novel difluorophthalic compounds and to the preparation of those compounds and related compounds. In particular, it relates to 3,5-difluorophthalic anhydride, imide, acid, and salts, esters, and half-esters of the acid and to the preparation of those compounds and the use of those compounds to prepare 3,5-difluorobenzoic acid and 3,5-difluorobenzene.

A variety of uses are known for 3,5-difluorobenzoic acid as a chemical intermediate. For example, it can be used as an intermediate in the synthesis of liquid crystal additions, fungicides, organo-tin antitumor compounds, insecticides, and quinolones. The compound 1,3-difluorobenzene can be used in the synthesis of antifungal agents, pharmaceuticals, dyes, and agrochemicals.

3,5-Difluorobenzoic acid has been prepared from 2,4-difluoroaniline. Bromination, followed by deamination with nitrous acid, led to 3,5-difluorobromobenzene. This was transformed by a Grignard reaction (magnesium, followed by the addition of $CO_2$). J. Org. Chem., 20 (1955) 1577. A second synthesis of 3,5-difluorobenzoic acid started with 3,5-difluorobromobenzene. This was treated with butyllithium followed by the addition of $CO_2$. CA(73): 77636. Both of these methods suffer from numerous steps and the unavailability of the starting material in commercial quantities.

1,3-Difluorobenzene can be prepared by diazotization of 1,3-diaminobenzene. This method requires a large number of steps and the starting material, 1,3-dichlorobenzene, is expensive and difficult to synthesize in large amounts. The diazotization reaction is somewhat dangerous due to the formation of intermediate diazo compounds and the use of sodium nitrite, a potentially explosive reagent, in the deamination reaction. In addition, the synthesis uses an expensive palladium catalyst in the reduction of the nitro group to the amine. A similar synthesis starts from the less expensive 1,2,4-trichlorobenzene, but still requires the use of an expensive palladium catalyst and a deamination reaction (Synth. Commun., 24(4), 529(1994)).

A second method for the synthesis of 1,3-difluorobenzene involves chlorodenitration of 2,4-difluoronitrobenzene, followed by catalytic hydrogenation of the resultant chlorodifluorobenzene. This method, although avoiding the problematic diazotization reactions, suffers due to the number of steps involved, as well as the use of chlorine gas and an expensive palladium catalyst (JP 03077836; CA 115(15):158695h).

SUMMARY OF THE INVENTION

We have discovered certain novel 3,5-difluorophthalic compounds which are useful in making pharmaceutical and agricultural intermediates such as quinolones. We have also discovered a method by which these compounds and successor compounds can be prepared. While previous methods of preparing fluorinated phthalic compounds required imidization in order to prevent decomposition (see, for example U.S. Pat. No. 4,769,493), we have discovered that with the 3,5-difluorophthalic compounds no imidization step is necessary. The elimination of the imidization step not only simplifies the overall process and reduces its cost, but also eliminates the production of by-products that would otherwise have to be disposed of. The method of this invention does not involve the use of expensive catalysts, does not require the use of potentially explosive nitrite reagents, does not require the formation of explosive diazo intermediates, and starts with a very inexpensive, commercially available material. An increased yield is also expected using the simplified process of this invention.

DESCRIPTION OF THE PREFERRED EMBODIMENT

The starting material for this invention is 3,5-dichlorophthalic anhydride, a known compound which can be prepared by reacting tetrachloro-N-alkylphthalimide with zinc and certain hydroxides as described in U.S. Pat. No. 5,086,188, herein incorporated by reference.

The first reaction of the process of this invention is a halogen exchange reaction in which 3,5-dichlorophthalic anhydride is reacted with a fluorinating agent to produce 3,5-difluorophthalic anhydride. Examples of suitable fluorinating agents include potassium fluoride, cesium fluoride, and tetrabutyl nitrogen fluoride. Potassium fluoride and cesium fluoride are preferred as they are commercial; potassium fluoride is particularly preferred as it is inexpensive. The amount of fluorinating agent used should be stoichiometric with the amount of 3,5-difluorophthalic anhydride up to about 25 mole percent in excess of stoichiometric.

The halogen exchange reaction can be performed in a dipolar aprotic solvent, in a non-polar solvent in the presence of a phase transfer catalyst, or in the absence of a solvent. It is preferable to use a dipolar solvent as that seems to result in the highest yield and it is easiest to isolate the product from a dipolar solvent. Examples of dipolar solvents include dimethylsulfoxide (DMSO), N-methylpyrrolidone (NMP), sulfolane, dimethylformamide, and N,N-dimethylacetamide (DMAC). The preferred dipolar solvent is sulfolane because it is inexpensive and is stable and its boiling point is above the reaction temperature. Examples of non-polar solvents include chlorobenzene, dichlorobenzene, trichlorobenzene, xylene, and toluene. Trichlorobenzene is preferred as its boiling point is above the reaction temperature. Examples of phase transfer catalysts include tetra-n-butylammonium chloride, tetra-n-butylammonium bromide, cetyltrimethylammonium bromide, cetyltrimethylammonium chloride, tetraphenylphosphonium bromide, tetraphenylphosphonium chloride, tetramethylammonium chloride, and tetramethylammonium bromide. The preferred phase transfer catalyst is tetra-n-butyl ammonium chloride or bromide because it is less expensive. About 1 to about 10 weight percent of a phase transfer catalyst (based on the weight of 3,5-dichlorophthalic anhydride) should be used. If a solvent is used, sufficient solvent should be present to solubilize the 3,5-difluorophthalic anhydride.

Typical reaction conditions are 140° to 190° C. for about 1 to about 2 hours. A gas chromatograph (GC) can be used to follow the reaction and determine when it is complete. The product can be isolated by filtering off the inorganic salts then pouring the filtrate into water. This results in the precipitation of the product which can be filtered and washed. The product, 3,5-difluorophthalic anhydride, is believed to be novel.

In the second reaction of the process of this invention, 3,5-difluorophthalic anhydride is reacted with excess water in the presence of a solvent at reflux for about 2 hours to form 3,5-difluorophthalic acid. Examples of suitable solvents that can be used include tetrahydrofuran (THF), dioxane, DMSO, sulfolane, and NMP. Tetrahydrofuran is preferred because it is readily available and has good dissolving properties. A weight ratio of solvent to water of about 75 to about 25 can be used. (There are many other ways to react the anhydride with water to form the di-acid, such as using water with hydrochloric acid, and these ways are well-known to those skilled in the art.) When the reaction is complete, the solvent is stripped under vacuum. This results in the precipitation of the product which can be isolated by filtration and washing.

Esters of the 3,5-difluorophthalic acid can be made by reacting the product with an alcohol as is well-known in the art. Half esters can be made by using stoichiometric quantities of alcohol. Salts of the di-acid or half ester can be made by reaction with inorganic hydroxides. These compounds have the formula

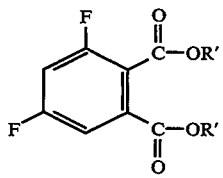

where R' is hydrogen, R, or M, R is alkyl, aryl, alkaryl, or aralkyl from $C_1$ to $C_{12}$, and M is a metal cation such as sodium, potassium, calcium, or magnesium; sodium and potassium are preferred as they are more soluble.

In the next reaction of this invention, the 3,5-difluorophthalic acid is decarboxylated. Decarboxylation can be accomplished in a solvent such as in NMP, DMAC, or quinoline.

The decarboxylation reaction is preferably conducted using a copper catalyst such as Cu, $Cu_2O$, CuO, $CuSO_4$, $CuCl_2$, CuCl, $CuF_2$, $Cu_2CO_3$, or $Cu(OH)_2$. In addition, halides and salts of Zn, Cd, Ag, and Ni can be used as catalysts. With a catalyst, the reaction can be conducted at about 125° to about 215° C., and preferably at 125° to 150° C. The catalyst shows some effect at concentrations as low as 1%. However, it is preferable to use between 5 and 10 percent by weight catalyst. At any point in the reaction, the proportion of starting materials to product can readily be judged by gas chromatography. Since the reaction is reproducible, once convenient conditions have been established for conducting the reaction, gas chromatographic analysis need not be routinely conducted.

Decarboxylation is preferably performed in NMP with 5 to 10% CuO by heating for 2 to 3 hours which fully converts the anhydride and the acid into the desired product, and no side products are detected by gas chromatography. The reaction can also be performed without a catalyst. However, if no catalyst is used, decarboxylation is conducted at 175° to 215° C. and the reaction is rather slow.

The difluorobenzoic acid product can be isolated from the reaction mixture by acidifying the mixture and extracting with a suitable solvent such as ethyl acetate or diethyl ether. Evaporation of the solvent yields crude, 3,5-difluorobenzoic acid which can be recrystallized and decolorized by using water and activated carbon. If one carboxyl group is removed, 3,5-difluorobenzoic acid is formed and if two carboxyl groups are removed, 1,3-difluorobenzene is formed.

Difluorobenzoic acid is the preferred product as it is more useful. Typically, a mixture of 3,5-difluorobenzoic acid and 1,3-difluorobenzene is produced, with harsher conditions resulting in a larger proportion of the 1,3-difluorobenzene. Separation of the two products can be accomplished by distillation by forming a salt and extracting the 1,3-difluorobenzene into an organic solvent. A 3,5-difluorophthalimide can be prepared according to the process of this invention by reacting 3,5-dichlorophthalic anhydride with a stoichiometric amount of a primary amine having the formula $H_2NR$ where R is alkyl, aryl, alkaryl, or aralkyl from $C_1$ to $C_{12}$. The preferred amines are methyl amine and aniline as they are inexpensive, readily available, and work well. This reaction can be run in acetic acid or in a solvent such as sulfolane. Sufficient solvent is used to dissolve the reactants, the reactants are heated to about 150° C., and the reaction is followed by gas chromatograph. When the reaction is complete, the reactant mixture is poured into water. This results in the precipitation of the 3,5-dichlorophthalimide, which can be filtered and washed. A 3,5-difluorophthalimide, believed to be a novel compound, having the formula

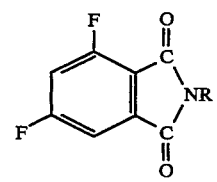

can be made by using 3,5-dichlorophthalimide in the hereinabove described halogen exchange reaction.

The following examples further illustrate this invention.

EXAMPLE 1

3,5-Dichlorophthalic acid (3.36 g, preparation given in Example 1 of U.S. Pat. No. 5,086,188) was refluxed with 10 mL of xylenes while the water generated from the cyclization was collected in a Barrett trap. After refluxing for 5 hours the reaction was cooled, and the xylenes were removed under vacuum. The resultant solids were dried overnight in a vacuum desiccator to give 2.32 g of 3,5-dichlorophthalic anhydride, mp 90° to 94° C.

EXAMPLE 2

Combined together under a nitrogen atmosphere were 5 g of 3,5-dichlorophthalic anhydride, 6.75 g of anhydrous potassium fluoride, and 0.5 g polyethylene glycol methyl ether (mw=200) sold by Aldrich as Carbowax MPEG 2000, which is used as a phase transfer catalyst. The reaction was heated to 195° C. for 4 hours. The reaction was cooled and 20 mL of methylene chloride was added. The inorganic salts were filtered off and washed with an additional aliquot of methylene chloride. The methylene chloride was removed under vacuum, and the residue (4.5 g) was distilled at 165° C. (3.5 mm Hg) to give 3.1 g of 3,5-difluorophthalic anhydride, mp 87° to 89° C. The purity was 97.5% as measured by GC.

EXAMPLE 3

Combined together under a nitrogen atmosphere were 3,5-dichlorophthalic anhydride (0.5 g), anhydrous potassium fluoride (0.54 g) and Carbowax MPEG 2000 (0.05 g). The reaction was stirred while being heated to 200° C. for 4 hours. The progress of the reaction was monitored by GC. After all the starting material had been consumed, a short path distillation apparatus was attached to the reaction flask and a vacuum was applied (3.5 mm Hg, 190° C.). Distilling over as a white solid was 3,5-difluorophthalic anhydride (0.19 g). The purity was 96.8% as measured by GC.

EXAMPLE 4

Combined together under a nitrogen atmosphere was 3,5-dichlorophthalic anhydride (0.25 g), anhydrous potassium fluoride (0.20 g) and 10 mL of dry sulfolane. The mixture was stirred and heated at 180° C. for 4 hours. Assay of the reaction at that time indicated the formation of 3,5-difluorophthalic anhydride (71.4%) and the mixed chlorofluorophthalic anhydrides (7.13%), along with other unidentified peaks.

EXAMPLE 5

Combined together under a nitrogen atmosphere was 3,5-dichlorophthalic anhydride (0.25 g), anhydrous potassium fluoride (0.21 g), tetraphenyl phosphonium bromide (0.026 g) and 2.5 mL of dry sulfolane. The mixture was stirred and heated at 140° to 160° C. for 5 hours. Assay of the reaction at that time indicated the formation of 3,5-difluorophthalic anhydride (63%) and the mixed chlorofluorophthalic anhydrides (7.13%), along with other unidentified peaks.

EXAMPLE 6

Combined together were 3,5-difluorophthalic anhydride (1.0 g) and 25 mL of a 75:25 (v/v) mixture of THF:water. The contents were heated for 6 hours at reflux. The THF and water were removed under vacuum, and the residue taken up in 50 mL of ethyl acetate. The ethyl acetate was dried with magnesium sulfate and filtered. Removal of the solvent under vacuum led to 1.09 g of 3,5-difluorophthalic acid, mp 155° to 157° C. as an off white solid.

EXAMPLE 7

Combined together were 3,5-difluorophthalic anhydride (0.5 g), copper (II) oxide (0.05 g) and NMP (5 mL). The contents were heated and stirred at 190° C. for 4 hours. After cooling to room temperature, the copper (II) oxide was filtered off and washed with ethyl acetate. The combined organic layers were placed on a rotary evaporator to remove the ethyl acetate. The remainder was added to 100 mL of water, in which a brown precipitate formed. The precipitate was filtered off and washed with an additional aliquot of water. The filtrate was extracted with 4×25 mL portions of ethyl acetate. The combined organics were washed with 3×25 Ml portions of water, dried with magnesium sulfate, filtered, and the ethyl acetate removed under vacuum. A total of 0.22 g of a pasty solid was recovered. $^{19}$F NMR analysis (comparison to known values) indicated that the solid consisted of a mixture of 3,5-difluorobenzoic acid (70%), 1,3-difluorobenzene (20%), with small amounts of other, unidentified materials.

EXAMPLE 8

In a series of three experiments, 0.5 g of 3,5-difluorophthalic acid was heated at 150° C. in each of 3.0 mL of NMP, DMAC, and DMSO for 4 hours. Assay of each of the reactions by GC indicated the formation of 3,5-difluorobenzoic acid being formed as the major product.

We claim:

1. A compound having the formula

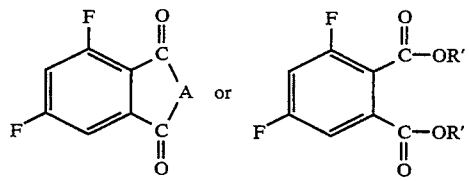

where A is O or NR, each R' is independently selected from hydrogen, R, or M, R is alkyl, aryl, alkaryl, or aralkyl from $C_1$ to $C_{12}$, and M is a metal cation.

2. A compound according to claim 1 which has the formula

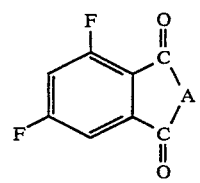

where A is 0.

3. A compound according to claim 1 which has the formula

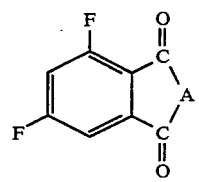

where A is NR.

4. A compound according to claim 3 wherein R is methyl.

5. A compound according to claim 3 wherein R is phenyl.

6. A compound according to claim 1 which has the formula

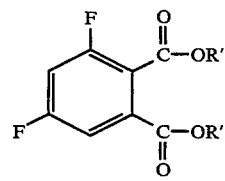

where R' is hydrogen.

7. A compound according to claim 1 which has the formula

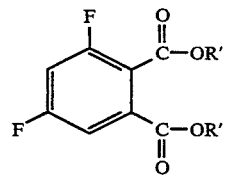

where R' is methyl.

8. A compound according to claim 1 which has the formula

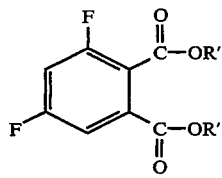

where R' is phenyl.

9. A compound according to claim 1 which has the formula

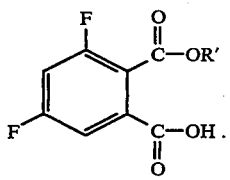

10. A compound according to claim 9 wherein R' is methyl.

11. A compound according to claim 9 wherein R' is phenyl.

12. A compound according to claim 1 which has the formula

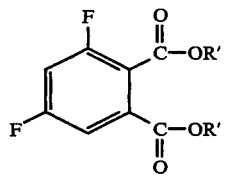

where R' is M and M is sodium.

13. A compound according to claim 1 which has the formula

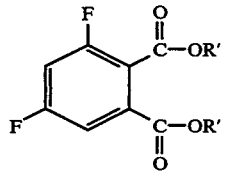

where R' is M and M is potassium.

14. A method of making a compound according to claim 1 which has the formula

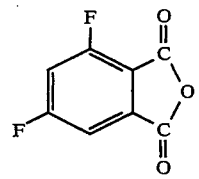

comprising reacting 3,5-dichlorophthalic anhydride with a fluorinating agent.

15. A method according to claim 14 wherein said fluorinating agent is KF or CsF.

16. A method of making a compound according to claim 1 which has the formula

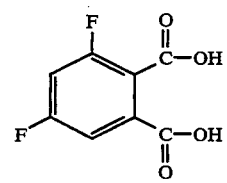

comprising
   (A) reacting 3,5-dichlorophthalic anhydride with a fluorinating agent to produce 3,5-difluorophthalic anhydride; and
   (B) reacting said 3,5-difluorophthalic anhydride with water.

17. A method according to claim 16 wherein said fluorinating agent is KF or CsF.

18. A method of making a mixture of 3,5-difluorobenzoic acid and 1,3-difluorobenzene comprising
   (A) reacting 3,5-dichlorophthalic anhydride with a fluorinating agent to produce 3,5-difluorophthalic anhydride;
   (B) reacting said 3,5-difluorophthalic anhydride with excess water to produce 3,5-difluorophthalic acid; and
   (C) decarboxylating said 3,5-difluorophthalic acid.

19. A method of making a mixture of 3,5-difluorobenzoic acid and 1,3-difluorobenzene comprising
   (A) reacting 3,5-dichlorophthalic anhydride with a fluorinating agent selected from the group consisting of KF and CsF in a stoichiometric amount to 25 mole % in excess of stoichiometric in a dipolar solvent, no solvent, or a non-polar solvent with a phase transfer catalyst at about 140° to about 190° C. to produce 3,5-difluorophthalic anhydride;
   (B) isolating said 3,5-difluorophthalic anhydride;
   (C) reacting said 3,5-difluorophthalic anhydride with excess water to produce 3,5-difluorophthalic acid;
   (D) isolating said 3,5-difluorophthalic acid; and
   (E) heating said 3,5-difluorophthalic acid in a dipolar aprotic solvent at about 125° to about 175° C. to form said 3,5-difluorobenzoic acid.

20. A method according to claim 19 wherein step (A) is performed in sulfolane or in a mixture of trichlorobenzene-and tetra-n-butylammonium chloride or tetra-n-butyl ammonium bromide.

* * * * *